United States Patent [19]

Porteous

[11] 4,321,038
[45] Mar. 23, 1982

[54] BRAIDED GINGIVAL RETRACTION CORD
[75] Inventor: Don D. Porteous, Los Angeles, Calif.
[73] Assignee: Van R Dental Products, Inc., Los Angeles, Calif.
[21] Appl. No.: 170,289
[22] Filed: Jul. 18, 1980
[51] Int. Cl.³ .............................................. A61C 5/14
[52] U.S. Cl. .................................... 433/136; 128/335.5
[58] Field of Search ............... 433/136, 40; 132/92 A; 128/335.5, 296, 269

[56] References Cited
U.S. PATENT DOCUMENTS

| | | | |
|---|---|---|---|
| 1,287,926 | 12/1918 | Ecqubert | 132/92 A |
| 1,985,667 | 12/1934 | Nelson et al. | 433/136 |
| 3,238,620 | 3/1966 | Robertson | 433/40 |
| 3,565,077 | 5/1968 | Glick | 128/335.5 |
| 3,618,609 | 11/1971 | Glick et al. | 128/296 |
| 3,949,755 | 4/1976 | Vauguois | 128/335.5 |
| 4,014,973 | 3/1977 | Thompson | 128/335.5 |
| 4,043,344 | 8/1977 | Landi et al. | 128/335.5 |
| 4,047,533 | 9/1977 | Perciaccante et al. | 128/335.5 |
| 4,205,680 | 6/1980 | Marshall | 128/296 |

*Primary Examiner*—Gene Mancene
*Assistant Examiner*—John J. Wilson
*Attorney, Agent, or Firm*—Donald Diamond

[57] ABSTRACT

A gingival tissue retraction cord is provided which comprises a suitably dimensioned, moderately firm, flexible, multistrand, braided, absorbent cord impregnated with an effective amount of gingival tissue retraction material. The retraction cord is adapted to be inserted into the gingival sulcus to effect retraction of gingival tissue.

24 Claims, 5 Drawing Figures

BRAIDED GINGIVAL RETRACTION CORD

BACKGROUND OF THE INVENTION

This invention relates to dental appliances and, more particularly, to gingival tissue retraction cords.

In dental therapeutics, it is often necessary to retract gingival tissue in order to prepare patients for taking impressions, setting crowns or effecting restorations.

In a widely used procedure for retracting gingival tissue, cotton cord, impregnated with a therapeutic preparation having astringent and hemostatic properties, is disposed about the tooth and placed into the gingival crevice for a limited time period to effect tissue displacement.

The fluid absorbent, cotton cord which is used in gingival retraction may be single or multiple strand of suitable cross-sectional area for dental purposes. The therapeutic preparations which may be absorbed onto the cotton cord to effect gingival retraction include, for example, racemic epinephrine hydrochloride and aluminum compounds such as potassium aluminum sulfate (alum). For a further discussion of gingival retraction with cotton cords as well as absorbent, resilient, circular rings composed of hard or soft leather, see U.S. Pat. No. 3,238,620 (Robertson, 1966).

Although the gingival retraction cord of the prior art is very effective as a tissue displacement device and agent, it has various negating characteristics. The mechanical handling of the prior art cord, which usually consists of twists of cotton strands or filaments has been somewhat difficult and awkward because of the pliable nature of the cord; in particular, it is difficult and awkward to thread the pliable cord between closely adjacent teeth and, where desired, to tie the loose ends prior to the insertion of the therapeutic cord into the gingival crevice. Also, unless the cord is packed into the gingival crevice with instrumentation which is applied in alignment with the twist, the strands or filaments can become unraveled during the packing step. The cotton twist cord may split during packing with the "L" shaped packing instrument whereby the horizontal arm of the instrument traverses the cord and reciprocal removal of the instrument through the body of the cord is somewhat difficult; and, in extreme cases, the traversal of the cotton twist cord by the relatively sharp packing instrument may result in severance of tooth attachment tissue. Since the cotton twist cord is highly pliable, it presents relatively small resistance to gum force and, while disposed in the gingival sulcus, it tends to flatten out thereby decreasing the spaced relationship between the tooth and the gum which can interfere with the taking of an impression. In addition, the tensile strength of the cotton twist cord is relatively weak as a result of which the cord tends to fray and leave therapeutically impregnated lint in the gingival sulcus which may cause tissue irritation.

Accordingly, the principal object of this invention is to provide a moderately firm, flexible, fluid absorbent, gingival retraction cord which (a) facilitates the circumdisposition of the cord about the tooth, (b) resists splitting during the packing of the cord into the gingival sulcus, (c) maintains its shape in the gingival sulcus and (d) is substantially fray resistant and lint free.

SUMMARY OF THE INVENTION

In accordance with one aspect of this invention, there is provided a gingival tissue retraction cord comprising a suitably dimensioned, moderately firm, flexible, multistrand, braided, absorbent cord impregnated with an effective amount of gingival tissue retraction material.

In accordance with a second aspect of this invention, there is provided a method for retracting gingival tissue which comprises inserting into the gingival sulcus a suitably dimensioned, moderately firm, flexible, multistrand, braided, absorbent cord impregnated with an effective amount of gingival tissue retraction material.

DETAILED DESCRIPTION

Figure 1:
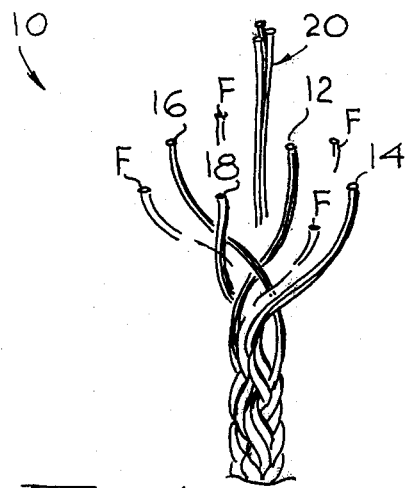
FIG. 1 is a partial, schematic, side elevational view of one embodiment of the braided retraction cord of this invention having 4 warp strands, 4 filling strands and 3 axial support strands.
Figure 1A:
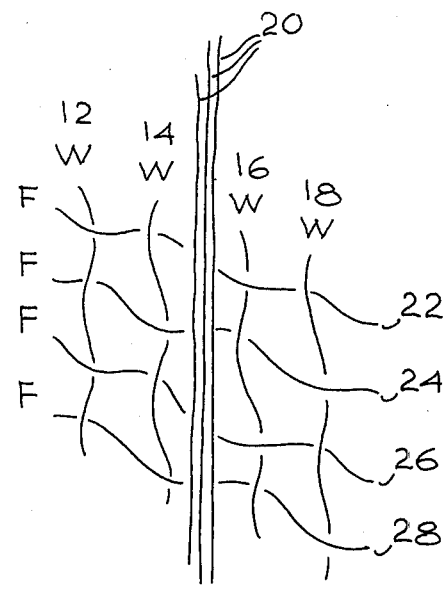
FIG. 1A is a diagramatic view of the cord depicted in FIG. 1 showing the filling strands successively passing over and then under adjacent warp strands and the warp strands successively passing over and then under adjacent filling strands.

Referring now to the drawings (wherein "F" identifies filling strands and "W" identifies warp strands) and, in particular, to FIGS. 1 and 1A, there is shown, in schematic and diagramatic views, a braided gingival retraction cord 10 having four warp strands, 12, 14, 16 and 18, three axial support strands 20 and four filling strands 22, 24, 26 and 28. As illustrated in FIG. 1A, the filling strands successively pass over and then under adjacent warp strands and the warp strands successively pass over and then under adjacent filling strands.

Figure 2:
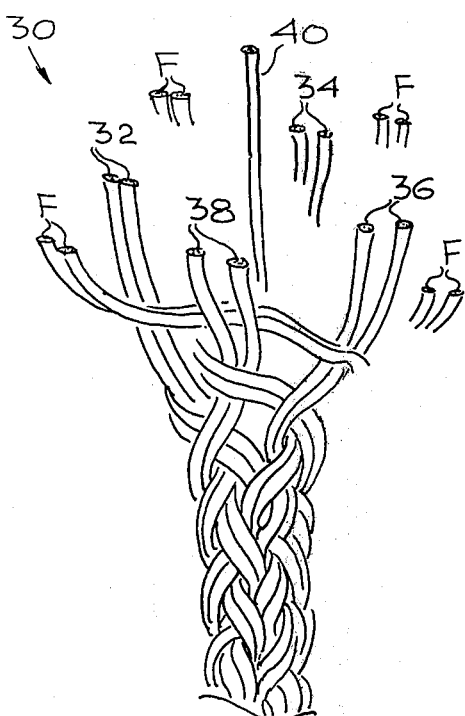
FIG. 2 is a partial, schematic, side elevational view of an alternative embodiment of the braided retraction cord of this invention having 4 pairs of warp strands, 4 pairs of filling strands and 1 axial support strand.
Figure 2A:
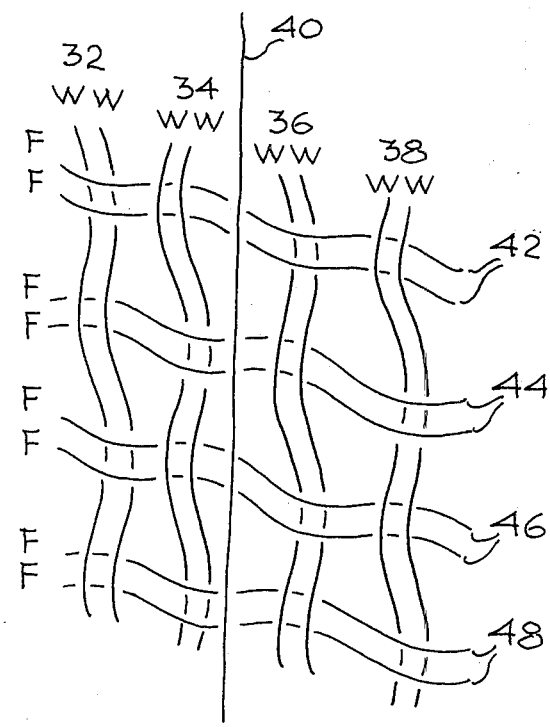
FIG. 2A is a diagramatic view of the cord depicted in FIG. 2 showing each pair of filling strands successively passing over and then under adjacent pairs of warp strands and each pair of warp strands successively passing over and then under adjacent pairs of filling strands.

With reference to FIGS. 2 and 2A, there is shown, in schematic and diagramatic views, a braided gingival retraction cord 30 having four pairs of warp strands 32, 34, 36 and 38 one axial support strand 40 and four pairs of filling strands 42, 44, 46 and 48. As depicted in FIG. 2A each pair of filling strands in this embodiment of the invention successively passes over and then under adjacent pairs of warp strands and each pair of warp strands successively passes over and then under adjacent pairs of filling strands.

The braided retraction cords of this invention comprise longitudinally disposed warp strands, transversely disposed filling strands and, advantageously, may include one or more axially or longitudinally disposed support strands. The individual strands comprise fluid absorbent yarns or thread of suitable size and weight. For example, the warp and filling strands may comprise No. 60/2 cotton thread which is composed of a double cotton filament twist having a length-pound ratio of 25,200 yards per pound and the axial support strands may comprise No. 40/2 cotton thread which is composed of a double cotton filament twist having a length-pound ratio of 16,800 yards per pound. The size and number of strands are so selected as to provide a gingival retraction cord having a diameter from about 0.015 to about 0.05 inch.

In one embodiment of this invention employing No. 60/2 cotton thread for all strands, the braided retraction cord has four warp strands, four filling strands, fifty two picks or plaits per linear inch, and a diameter of about 0.5 mm (0.02 in.). In a second embodiment of this invention employing No. 60/2 cotton thread for the warp and filling strands and No. 40/2 cotton thread for the axial support strands, the braided retraction cord has four warp strands, three axial support strands, four filling strands, thirty eight picks or plaits per linear inch, and a diameter of about 0.635 mm (0.025 in.). In a third embodiment of this invention employing No. 60/2 cotton thread for the warp and filling strands and No. 40/2 cotton thread for the axial support strand, the braided retraction cord has four pairs of warp strands, one axial support strand, four pairs of filling strands, twenty seven picks or plaits per linear inch, and a diameter of about 0.762 mm (0.030 in.).

The braided retraction cord generally has from about 24 to about 60 picks or plaits per linear inch with the number of picks or plaits per linear inch being inversely proportional to the increasing diameter of the cord and being so selected as to provide a flexible cord having a relatively firm body.

One or more of the filling strands may be a suitably dyed strand which can impart a color code to the braided retraction cord to indicate size or for other identification purposes.

The braided retraction cord of this invention may advantageously include from one to three or more axial support strands which, beneficially, enable the substantially annular cord to resist flattening in the gingival sulcus where the gum tissue exerts a positive force and pressure in the direction of the tooth. This resistance of the cord to flattening distortion under use conditions is highly desirable since flattening of the gingival retraction cord can interfere with the taking of an impression.

Figure 3:
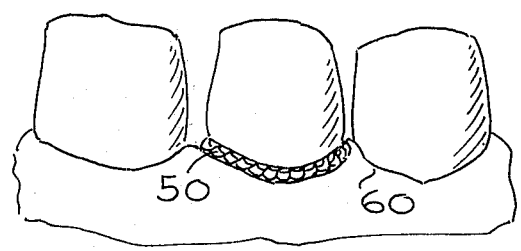
FIG. 3 is a schematic, perspective view showing the braided gingival retraction cord of this invention disposed about a tooth and packed into the gingival crevice.

As schematically illustrated in FIG. 3, the braided retraction cord 50, which comprises interlaced and entwined warp and filling strands, is readily and easily disposed about the tooth and packed into the gingival sulcus 60. The interlaced and entwined strands which form the braided retraction cord resist unraveling and untwisting during the packing step and, at the same time, resist splitting and transversing of the cord by the packing instrument. This latter feature is very significant because traversal of the cord by the relatively sharp packing tool can result in cutting or, in extreme case, severance of tooth attachment tissue. In addition, the braided retraction cord resists fraying and is substantially lint free as a result of which substantially no chemically impregnated lint is left in the gingival sulcus upon removal of the braided cord from the sulcus.

The braided retraction cord may be fabricated by using any suitable braiding machine as, for example, a Wardwell rapid braider having two carrier tiers with eight carriers in each tier as well as central dispensing carriers. By suitably spacing a selected number of thread spools on the upper and lower tiers, a braided cord is obtained in which the filling strands successively pass over and then under adjacent warp strands and warp strands successively pass over and then under adjacent filling strands as diagramatically shown in FIG. 1A, or, in an alternative embodiment, a braided cord is obtained in which pairs of filling strands successively pass over and then under adjacent pairs of warp strands and pairs of warp strands pass over and then under adjacent pairs of filling strands as diagramatically shown in FIG. 2A.

Following the fabrication of the braided cord, it is passed through an impregnating solution containing a suitable concentration of retraction material such as epinephrine, alum, aluminum chloride, or mixtures thereof to saturate the cord with the solution. In an illustrative embodiment, the braided cord is passed through and saturated with a retraction solution containing 8% racemic epinephrine and 7% aluminum potassium sulfate. Upon completion of the soaking and saturation step, the braided cord is dried to remove the fluid carrier. The dried cord may be wound in spool form and packaged in glass dispensers.

For retraction of gingival tissue, the dental practioner passes the treated cord around the neck of the tooth and packs its into the gingival sulcus. Normal tissue moisture, water or gingival retraction solutions activate the impregnated braided cord to retract the gingival tissue.

While in the foregoing description and accompanying drawings there has been shown and described the preferred embodiment of this invention, it will be understood, of course, that minor changes may be made in the details of construction as well as in the combination, arrangement and composition of parts, without departing from the spirit and scope of the invention as claimed.

That which is claimed is:

1. A gingival tissue retraction cord comprising a suitably dimensioned, moderately firm, flexible, multi-strand, braided, absorbent cord impregnated with an effective amount of gingival tissue retraction material.

2. The braided retraction cord of claim 1 wherein the braided strands comprise filling strands and warp strands with said filling strands successively passing over and then under adjacent warp strands and said warp strands successively passing over and then under adjacent filling strands.

3. The braided retraction cord of claim 2 which includes 4 warp strands and 4 filling strands.

4. The braided retraction cord of claim 2 which includes axially disposed support strand means.

5. The braided retraction cord of claim 4 which includes 4 warp strands, 4 filling strands and 3 axially disposed support strands.

6. The braided retraction cord of claim 1 wherein the braided strands comprise a plurality of pairs of filling strands and a plurality of pairs of warp strands with each of said pairs of filling strands successively passing over and then under adjacent pairs of warp strands and each of said pairs of warp strands successively passing over and then under adjacent pairs of filling strands.

7. The braided retraction cord of claim 6 which includes axially disposed support strand means.

8. The braided retraction cord of claim 7 which includes 4 pairs of warp strands, 4 pairs of filling strands and 1 axially disposed support strand.

9. The braided retraction cord of claim 1 wherein said cord has a diameter from about 0.015 to about 0.05 inch.

10. The braided retraction cord of claim 9 wherein said cord has from about 24 to about 60 picks per inch with the number of picks per inch being inversely proportional to the increasing diameter of the cord and being so selected as to provide a moderately firm, flexible cord.

11. The braided retraction cord of claim 9 wherein said cord has from 3 to about 24 strands.

12. The braided retraction cord of claim 1 wherein the gingival tissue retraction material is epinephrine, alum, aluminum chloride or mixtures thereof.

13. A method for retracting gingival tissue which comprises inserting into the gingival sulcus a suitably dimensioned, moderately firm, flexible, absorbent, multistrand, braided, retraction cord impregnated with an effective amount of gingival tissue retraction material.

14. The method of claim 13 wherein the braided strands of the retraction cord comprise filling strands and warp strands with said filling strands successively passing over and then under adjacent warp strands and said warp strands successively passing over and then under adjacent filling strands.

15. The method of claim 14 wherein the braided retraction cord includes four warp strands and four filling strands.

16. The method of claim 14 wherein the braided retraction cord includes axially disposed support strand means.

17. The method of claim 16 wherein the braided retraction cord includes four warp strands, four filling strands and three axially disposed support strands.

18. The method of claim 13 wherein the braided strands comprise a plurality of pairs of filling strands and a plurality of pairs of warp strands with each of said pairs of filling strands successively passing over and then under adjacent pairs of warp strands and each of said pairs of warp strands successively passing over and then under adjacent pairs of filling strands.

19. The method of claim 18 wherein the braided retraction cord includes axially disposed support strand means.

20. The method of claim 19 wherein the braided retraction cord includes four pairs of warp strands, four pairs of filling strands and one axially disposed support strand.

21. The method of claim 13 wherein the braided retraction cord has a diameter from about 0.015 to about 0.05 inch.

22. The method of claim 21 wherein the braided retraction cord has from about 24 to about 60 picks per inch with the number of picks per inch being inversely proportional to the increasing diameter of the cord and being so selected as to provide a moderately firm, flexible cord.

23. The method of claim 21 wherein the braided retraction cord has from 3 to about 24 strands.

24. The method of claim 13 wherein the braided retraction cord is impregnated with epinephrine, alum, aluminum chloride or mixtures thereof.

* * * * *